(12) United States Patent
Ghazizadeh et al.

(10) Patent No.: US 6,551,354 B1
(45) Date of Patent: Apr. 22, 2003

(54) ACCOMMODATING INTRAOCULAR LENS

(75) Inventors: Massoud Ghazizadeh, Laguna Hills, CA (US); Joseph I. Weinschenk, III, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/522,326

(22) Filed: Mar. 9, 2000

(51) Int. Cl.$^7$ .................................................. A61F 2/16
(52) U.S. Cl. ..................... 623/6.43; 623/6.34; 623/6.39; 623/6.44
(58) Field of Search ................................ 623/6.33, 6.34, 623/6.44, 6.43, 6.37, 6.39, 6.4, 6.49

(56) References Cited

U.S. PATENT DOCUMENTS

| | | | |
|---|---|---|---|
| 1,483,509 | A | 2/1924 | Bugbee |
| 2,129,305 | A | 9/1938 | Feinbloom |
| 2,274,142 | A | 2/1942 | Houchin |
| 2,405,989 | A | 6/1946 | Beach |
| 2,511,517 | A | 6/1950 | Spiegel |
| 3,031,927 | A | 5/1962 | Wesley |
| 3,034,403 | A | 5/1962 | Neefe |
| RE25,286 | E | 11/1962 | DeCarle |
| 3,210,894 | A | 10/1965 | Bentley et al. |
| 3,227,507 | A | 1/1966 | Feinbloom |

(List continued on next page.)

FOREIGN PATENT DOCUMENTS

| | | |
|---|---|---|
| AU | 3225789 | 10/1989 |
| DE | 3246306 | 6/1984 |
| EP | 0246216 | 11/1987 |
| EP | 0329981 | 8/1989 |
| EP | 337390 | 10/1989 |
| EP | 0342895 | 11/1989 |
| EP | 0351471 | 1/1990 |
| EP | 0566170 | 10/1993 |
| EP | 0691109 | 1/1996 |
| EP | 939016 | 1/1996 |

(List continued on next page.)

OTHER PUBLICATIONS

Menezo et al J Cataract Refract Surg 24, Aug. 1998.
Fechner et al J Cataract Refract Surg 24, Jan. 1998.
World Optics Inc. Opthalmology Times, Mar. 15, 1995.
Lolab Corp. Ophthalmology Times, Mar. 15, 1995.
Universe IOL Center, Ocular Surgery News Int'l, No date given.
Hanita Lenses, Ocular Surgery News Int'l, No date given.
Alcon Surgical, Alcon Laboratories, No date given.
Mediphacos Ltda. Ocular Surgery News,Int'l, No date given.
Storz Ophthalmics Inc. Model LIZZUV ACL. No date given.
Opthamed Inc. OMAC–260, No date given.
Chaulin–Opsia, Azunte ACL(0459) No date given.
AMO Specs, Model AC–218, 1992.

(List continued on next page.)

*Primary Examiner*—David J. Isabella
*Assistant Examiner*—Urmi Chattopadhyay
(74) *Attorney, Agent, or Firm*—Stout, Uxa, Buyan & Mullins, LLP; Frank J. Uxa; Peter Jon Gluck

(57) ABSTRACT

An intraocular lens includes an optic for focusing light and a movement assembly coupled to the optic. The movement assembly is adapted to cooperate with the eye to effect accommodating movement of the optic. The movement assembly includes a plurality of movement members each with a proximal region coupled to the optic and an enlarged distal region. The enlarged distal region may be integral with the proximal region, or may be mechanically coupled thereto.

24 Claims, 2 Drawing Sheets

U.S. PATENT DOCUMENTS

| | | |
|---|---|---|
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,629,460 A * | 12/1986 | Dyer ........................ 623/6.53 |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Isnetaki et al. |
| RE32,525 E | 10/1987 | Pannu |
| 4,702,244 A | 10/1987 | Mazzocco |
| 4,704,016 A | 11/1987 | DeCarle |
| 4,720,286 A | 1/1988 | Bailey et al. |
| 4,725,278 A * | 2/1988 | Shearing ........................ 623/6 |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,888,012 A | 12/1989 | Horn et al. |
| 4,888,015 A | 12/1989 | Domino |
| 4,890,912 A | 1/1990 | Visser |
| 4,890,913 A | 1/1990 | DeCarle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Milge et al. |
| 4,976,732 A | 12/1990 | Vorosmarthy |
| 4,990,159 A | 2/1991 | Kraft |
| 4,994,082 A | 2/1991 | Richards et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,026,396 A | 6/1991 | Darin |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,549,760 A | 8/1996 | Becker |
| 5,562,731 A | 10/1996 | Cumming |
| 5,578,081 A | 11/1996 | McDonald |
| 5,607,472 A | 3/1997 | Thompson |
| 5,609,630 A * | 3/1997 | Crozafon ........................ 623/6 |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,814,103 A | 9/1998 | Lipshitz et al. |
| 5,843,188 A | 12/1998 | McDonald |
| 5,876,442 A | 3/1999 | Lipshitz et al. |
| 6,013,101 A | 1/2000 | Israel |
| 6,096,078 A | 8/2000 | McDonald |
| 6,176,878 B1 | 1/2001 | Gwon et al. |
| 6,217,612 B1 | 4/2001 | Woods |
| 6,224,628 B1 * | 5/2001 | Callahan et al. ............. 623/6.4 |
| 6,387,126 B1 * | 5/2002 | Cumming .................. 623/6.37 |

FOREIGN PATENT DOCUMENTS

| | | |
|---|---|---|
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |

| | | |
|---|---|---|
| GB | 2192291 | 1/1988 |
| GB | 2215076 | 9/1989 |
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |
| WO | 9416648 | 8/1994 |
| WO | 9503783 | 2/1995 |
| WO | 9615734 | 5/1996 |
| WO | 9625126 | 8/1996 |
| WO | 9743984 | 11/1997 |
| WO | 0066040 | 11/2000 |
| WO | 0134067 | 5/2001 |

OTHER PUBLICATIONS

Chiron, Clemente Optifit Modell SPSP525 Brochure Translation, Dec. 1998.

Chrion Vision, Nunta Ma20, 1997.

Partial Program re: ASCRS Symposium, Showing Video Tape Shown Between Apr. 10–14, 1999.

Thornton, Accommodation in Pseudophakia, 25, pp. 159–162.

Video Tape "New Elliptical Acco. IOL for Cataract Surgery", Shown at ASCRS Symposium on Apr. 10, 1999. (Video Enclosed).

* cited by examiner

ACCOMMODATING INTRAOCULAR LENS

BACKGROUND OF THE INVENTION

The present invention relates to intraocular lenses (IOLs). More particularly, the present invention relates to IOLs which are adapted to provide accommodating movement in the eye.

The human visual system includes the eyes, the extraocular muscles which control eye position within the eye socket, the optic and other nerves that connect the eyes to the brain, and particular areas of the brain that are in neural communication with the eyes. The visual system is particularly well adapted for the rapid and precise extraction of spatial information from a field of view which is accomplished by analyzing the continuously changing patterns of radiant flux impinging upon the surfaces of the eyes.

Image formation is greatly complicated by the movement of the eyes within the head, as well as by the movement of both eyes and the head relative to the external sea of radiant energy. Visual input is ordinarily sampled by discrete momentary pauses of the eyes called fixations, interrupted by very rapid ballistic motions known as saccades which bring the eye from one fixation position to the next. Smooth movements of the eyes can occur when an object having a predictable motion is available to be followed.

Each eye forms an image upon a vast array of light sensitive photoreceptors of the retina. The cornea is the primary refracting surface which admits light through the anterior part of the outer surface of the eye. The iris contains muscles which alter the size of the entrance port of the eye, or pupil. The crystalline lens has a variable shape, under the indirect control of the ciliary muscle. Having a refractive index higher than the surrounding media, the crystalline lens gives the eye a variable focal length, allowing accommodation to objects at varying distances from the eye.

Much of the remainder of the eye is filled with fluids and materials under pressure which help the eye maintain its shape. For example, the aqueous humor fills the anterior chamber between the cornea and the iris, and the vitreous humor fills the majority of the volume of the eye in the vitreous chamber. The crystalline lens is contained within a third chamber of the eye, the posterior chamber, which is positioned between the anterior and vitreous chambers.

The human eye is susceptible to a score or more of disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replace with an intraocular lens, or IOL.

While restoring vision, conventional IOLs have limited ability for accommodation (i.e., the focusing on near objects). This condition is known as presbyopia. To overcome presbyopia of an IOL, a patient may be prescribed eyeglasses. Alternative attempts in the art to overcome presbyopia focus on providing IOLs with accommodation ability. Accommodation may be accomplished by either changing the shape of the IOL, e.g., to become more convex to focus on near objects, or by moving the IOL along its optical axis. For example, a number of these approaches bias an IOL to be located in the most posterior position of the posterior chamber of the eye under rest conditions. When near focus is required, the ciliary muscle contracts, and the IOL moves forwardly, which is known as positive accommodation. In the absence of ciliary muscle contraction, the IOL is biased rearwardly to the most posterior position. While these approaches may provide limited accommodation, the posterior bias and the configuration of the IOL prevent sufficient forward axial movement required for full-range accommodation.

In view of the foregoing, it would be beneficial in the art to provide IOLs adapted for sufficient accommodation to reduce significantly or to overcome the effects of presbyopia.

SUMMARY OF THE INVENTION

New intraocular lenses (IOLs) effective to provide accommodation have been discovered. The present IOLs provide effective accommodation using one or more optics. The IOLs of the invention also inhibit cell growth, particularly epithelial cell growth, onto the optics of the IOLs. The IOLs of the present invention are configured, and preferably promote cellular and fibrous growth to desired regions of the IOL, to increase the amount of force exerted by the eye against the IOLs to increase the amount of accommodation achieved. The present IOLs are relatively straightforward in design, can be produced using conventional IOL manufacturing procedures and can be inserted or implanted in eyes, e.g., human eyes, using surgical techniques which are the same as or analogous to such techniques used with conventional IOLs.

According to one aspect of the invention, an intraocular lens is provided which includes an optic for focusing light on a retina and a movement assembly coupled to the optic. The movement assembly is adapted to cooperate with the eye to effect accommodating movement of the optic. The movement assembly includes a movement member with a proximal region coupled to the optic. The movement member, and in particular the proximal region of the movement member, extends radially outwardly from the optic and includes an enlarged distal region with a contact surface adapted to be in contact with a peripheral region of a capsular bag of an eye.

One of the advantages of the present invention is that the IOL is held within, preferably attached to, the capsular bag. More specifically, the contact surface of the enlarged distal region may have an axial length of at least about 1 mm. Therefore, depending upon the radius of the IOL, the contact surface has a relatively large surface area with which to contact the capsular bag.

The contact of the IOL with the capsular bag is further enhanced by disposing the enlarged distal region in an angled manner relative to the proximal region of the member. Preferably, the contact surface is substantially parallel to the optical axis of the IOL. The relatively large contact surface is effective in maintaining the position of the IOL particularly directly following implantation and, on a long term basis, is effective in increasing the amount of accommodation provided by the IOL.

The relatively large surface area of the contact surface also promotes cellular and fibrous growth to or onto this region of the IOL, which further holds and retains the IOL within the capsular bag and increases the amount of force that may be exerted through the capsular bag onto the IOL to provide accommodation, as desired. Post-operative cellular and fibrous growth of the interior of the capsular bag to the enlarged distal region of the movement assembly may, and preferably does, enable the IOLs of the present invention to function substantially analogous to a natural crystalline lens.

To further facilitate this post-operative cellular growth, the enlarged distal region may include a plurality of depressions or through holes. Each of the through holes preferably provides increased growth of cells and fibrin onto the enlarged distal region or regions of the IOL. Accordingly, the IOL is very effectively attachable, preferably substantially permanently attachable, to the capsular bag. This attachment of the IOL to the capsular bag facilitates the axial movement of the IOL in direct response to changes in the capsular bag, therefore providing effective accommodation, analogous to a natural crystalline lens.

The IOLs of the present invention preferably inhibit unwanted posterior capsule opacification (PCO) of the optic. Thus, the distal region or regions of the movement assembly preferably is or are joined to the proximal region or regions so that one or more sharp edges, that is preferably edges which occur at discontinuities (rather than at smooth, continuous transitions) when viewed by the naked human eye, are present between the joined proximal and distal regions. Such sharp edges have been found to advantageously inhibit PCO by inhibiting the growth of cells, for example, epithelial cells, from the capsular bag onto the optic of the present IOLs.

To further enhance the accommodating movement of the present IOLs in cooperation with the eye, the movement assembly preferably is positioned relative to the optic so that, with the IOL at rest, that is with no forces acting on the IOL to effect accommodation, the proximal region of the movement member is positioned at an angle other than 90° relative to the central optical axis of the optic. In a very useful embodiment, the optic, in the rest position as noted above, is anteriorly vaulted. Also, the movement member or members preferably include a hinge, or a plurality of hinges, located on the proximal region or regions of the movement members, more preferably closer to the optic than to the distal region or regions. Each of these features, either individually or any combination thereof, is effective to further facilitate the movement of the optic to provide the desired amount of accommodation.

According to another aspect of the invention, the movement assembly includes a plurality of movement members, preferably spaced apart, for example, radially or circumferentially spaced apart, from each other. Each movement member includes a proximal region coupled to the optic and an enlarged distal region, for example, as described elsewhere herein. The enlarged distal regions each have a contact surface adapted to be in contact with a peripheral region of a capsular bag of an eye. In addition, the enlarged distal regions may be configured such that the contact surfaces are substantially coaxial with the optical axis of the optic.

A plurality of spacer or cut-out regions preferably are located between radially or circumferentially adjacent movement members. Such cut-out regions are effective to prevent buckling of the IOL during accommodating movement in the eye. Such spacers or cut-out regions may be open. In one useful embodiment each of such regions is at least partially covered with or by a structural material having increased flexibility relative to the movement members. Thus, the IOL is prevented from buckling while, at the same time the structural material is effective to at least inhibit cell growth from the capsular bag onto the optic. This structural material may have the same chemical make-up as the proximal regions of the movement members and have a reduced thickness relative to the proximal regions to provide the increased flexibility.

Another advantage of the present IOLs is that a second optic may be provided. According to this multi-optic embodiment, the secondary optic may be coupled to the enlarged distal region or regions with one or more secondary movement members.

In one useful embodiment, the enlarged distal region or regions of the movement member or members are provided with a groove or grooves. The secondary movement member or members are adapted to fit into the groove or grooves, thereby holding the second optic in position in the eye. Alternately, the second optic and secondary movement members may be formed integrally with the optic/movement assembly combination.

In a further useful embodiment of present invention, the enlarged distal region or regions of the movement member or members are mechanically coupled to the perspective proximal regions. In one particular embodiment, an intraocular lens comprises a plurality of arcuate segments mechanically coupled (e.g., adhered) to an integrally formed optic and radially outward movement members. The arcuate segments may have one or more grooves for receiving one or more movement members, thus forming either a one-optic or a two-optic system.

The second optic preferably has an optical power, or even substantially no optical power. The combination of the optic and second optic together preferably provides the optical power required or desired by the patient in whose eye the IOL is to be implanted. For example, the second optic can have a plano or substantially plano optical power or a relatively highly negative optical power, for example, between about −30 diopters to about −10 diopters, as desired. The second optic preferably is located posterior of the optic. In one useful embodiment, the second optic, in the eye, is substantially maintained in contact with the inner posterior wall of the capsular bag. This feature inhibits or reduces the risk of cell growth or migration from the capsular bag into the second optic. The second optic in such a posterior position often has only a relatively restricted, if any, amount of axial movement. Such a posterior second optic preferably is posteriorly vaulted, with the IOL in the rest position as described elsewhere herein, to facilitate maintaining the posterior face of the second optic in contact with the inner posterior face of the capsular bag.

Any and all of the features described herein and combinations of such features are included within the scope of the present invention provided that the features of any such combination are not mutually inconsistent.

Additional aspects, features, and advantages of the present invention are set forth in the following description and claims, particularly when considered in conjunction with the accompanying drawings in which like parts bear like reference numbers.

DETAILED DESCRIPTION OF THE DRAWINGS

Figure 1:
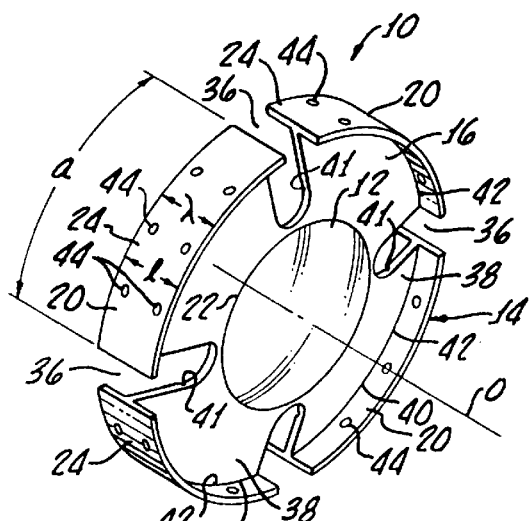
FIG. 1 is a perspective of an intraocular lens (IOL) according to an exemplary embodiment of the present invention, particularly illustrating an anterior side of the IOL.

Referring to the drawings in more detail, an intraocular lens (IOL) 10 according to an exemplary embodiment of the present invention is illustrated in FIG. 1. Exemplary IOL 10 includes an optic 12 and a movement assembly 14 coupled to the optic 12. The optic 12, which has an optical axis O, is adapted to focus light on a retina of an eye. The movement assembly 14 of exemplary IOL 10 is adapted to cooperate with an eye to effect accommodating movement of the optic 12, which is discussed in detail below.

Exemplary movement assembly 14 includes a member 16 with a proximal region 18 and an enlarged distal region 20. The terms "proximal" and "distal" are used herein with respect to the distance from the optical axis O. The proximal region 18 is coupled to the optic 12 at a periphery 22 of the optic. The member 16 extends radially outwardly from the optic 12 and the proximal region 18 to the enlarged distal region 20. With additional reference to FIG. 2, the enlarged distal region 20 has a contact surface 24 which is adapted to be in contact with a peripheral region 26 of a capsular bag 28 of an eye 30.

Figure 2:
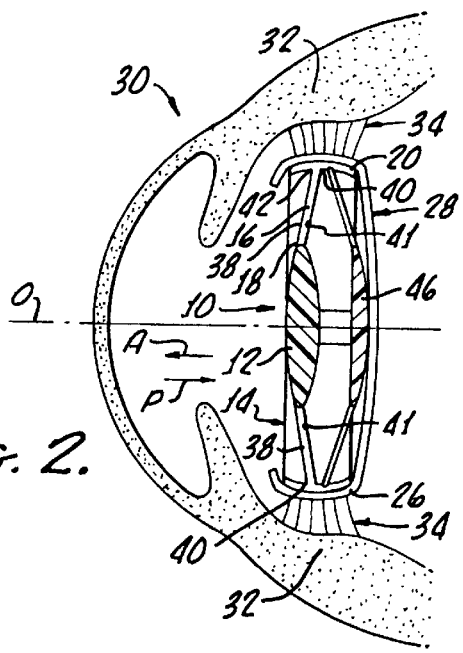
FIG. 2 is a fragmentary cross-sectional view of an eye in which an IOL configured in accordance with the present invention has been implanted.

Briefly describing the anatomy of the eye 30 with reference to FIG. 2, the capsular bag 28 is connected to a ciliary muscle 32 by suspensory ligaments or zonules 34. The ciliary muscle 32 is the prime mover in accommodation, i.e., in adjusting the eye 30 to focus on near objects. The zonules 34 retain the lens in position and are relaxed by the contraction of the ciliary muscle 32, thereby allowing a natural crystalline lens to become more convex.

Applying this anatomy to the present invention, exemplary IOL 10 is configured to facilitate movement of the optic 12 in response to the action of the ciliary muscle 32 and the zonules 34. When near vision is needed, the ciliary muscle 32 contracts, and the zonules 34 relax and reduce the equatorial diameter of the capsular bag 28, thereby moving the optic 12 anteriorly as indicated by arrow A in FIG. 2. This anterior movement of the optic 12 increases or amplifies the amount of positive (i.e., near) accommodation of the optic 12. Conversely, when the ciliary muscle 32 relaxes, the zonules 34 constrict and increase the equatorial diameter of the capsular bag 28, thus moving the optic posteriorly as indicated by arrow P.

For human implantation, exemplary IOL 10 may be configured such that the amount of positive or near accommodation is preferably at least about 1 diopter and may range up to 3.5 diopters or more. Further, exemplary IOL 10 may be configured to provide at least about 1.5 mm or 2 mm of axial movement anteriorly in the eye with about a reduction of about 1 mm in the equatorial diameter of the capsular bag 28 caused by the ciliary muscle 32 and the zonules 34.

As mentioned, the enlarged distal region 20 of the movement assembly 14 is adapted to be in contact with the peripheral region 26 of the capsular bag 28. In accordance with the invention, the contact surface 24 of the enlarged distal region 20 has a relatively large surface area. In other words, it is preferable to maximize the surface area of the contact surface 24 while maintaining the ability of the IOL 10 to be received within the capsular bag 28. By maximizing the surface area with which the IOL 10 contacts the capsular bag 28, the IOL 10 of the present invention effectively responds to changes in force exerted by the capsular bag 26 on the lens 10, thereby maximizing axial movement of the optic 12. In addition to the advantage of maximizing axial movement, the contact surface 24 of the enlarged distal region 20 also provides a large surface area to be subject to cellular and fibrous growth, which will be discussed in more detail below.

According to the exemplary embodiment of the invention shown in FIG. 1, the enlarged distal region 20 may be described as a plurality of peripheral arcuate bands with the contact surface 24 comprising the distal surface of each band. Each of the arcuate bands of the enlarged distal region 20 extends axially and has a length l, which will be discussed in more detail below. Each of the enlarged distal regions 20 may extend axially in a substantially parallel relationship with the optical axis O or, alternatively, may be arcuate in the axial direction such that the length l is an arc length λ (both symbols illustrated in FIG. 1 on one of the contact surfaces 24).

Regarding exemplary IOL 10 in more detail, the movement assembly 14 may include a plurality of cut-out regions 36 (e.g., four), thereby defining a corresponding plurality of spokes or haptic members 38. Each of the haptic members 38 includes a respective portion of the enlarged distal region 20 of the member 16 of the assembly 14. The cut-out regions 36 provide spatial relief when the ciliary muscle 32 contracts, thereby preventing buckling of the optic 12 during accommodation. To prevent posterior capsule opacification (PCO), each of the cut-out regions 36 may be filled with the same material from which the optic 12 is made.

Regarding the haptic members 38 in more detail, the haptic members 38 as shown in the exemplary embodiment of FIG. 1 may be substantially flat in configuration, flaring outwardly like pieces of a pie. The haptic members 38 desirably lie in planes angled with respect to the optical axis O to promote anterior movement, as further explained below. As mentioned, it is preferable to include four haptic members 38, such that each haptic member 38 may extend through nearly 90°, which extent is dependent upon the size of the cut-out regions 36.

To further enhance axial movement and accommodation, the haptic members 38 of exemplary movement assembly 14 may be angulated such that the optic 12 is positioned anterior to respective intersections 40 of the haptic members 38 and the enlarged distal regions 20, which is particularly shown in FIG. 2. For the purposes of this description, this angled configuration of the haptic members 38 is called "anterior angulation." By angulating the haptic members 38 in this anterior manner, the movement assembly 14 is biased to move the optic 12 toward the anterior of the eye 30 when the ciliary muscle 32 contracts. Furthermore, the anterior angulation of the haptic members 38 ensures that the optic 12 moves in the anterior direction when the ciliary muscle 32 contracts.

Figure 3:
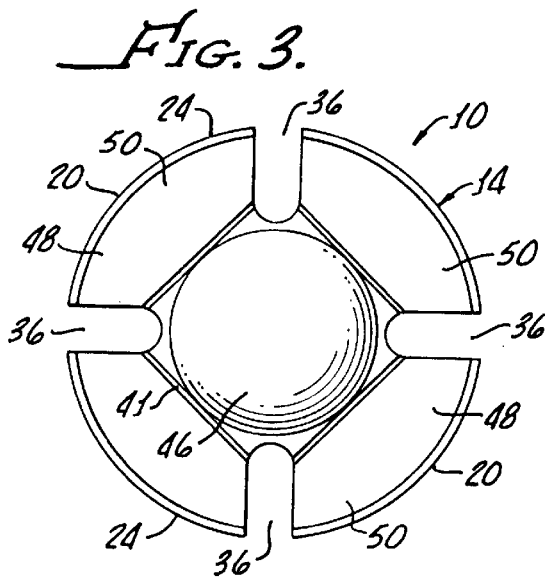
FIG. 3 is a plan view of an intraocular lens (IOL) of the invention, particularly illustrating a posterior side of the IOL.

With continued reference to FIGS. 1 and 2 and additional reference to FIG. 3, accommodation may be further enhanced by providing each of the haptic members 38 with a groove 41 formed in a posterior side thereof. The grooves 41 define an area of reduced thickness of each haptic member 38, thereby biasing the haptic members 38 to flex or pivot at the grooves 41. With such a construction, the grooves 41 accommodate flexing of the haptic members 38 in the anterior direction. As an alternative to the linear embodiment shown in FIG. 3, the grooves 41 may be arcuate and concentric with respective contact surfaces 24.

Axial movement may be further facilitated by providing a hinge 42 at the interior intersection 40 of each haptic member 38 with the respective portion of the enlarged distal region 20. The hinges 42 enhance the pivoting of the haptic members 38 relative to the enlarged distal region 20 when the ciliary muscle 32 contracts. In addition, each hinge 42 may be configured as a discontinuity, preferably a sharp edge, to retard or prevent cellular growth onto the haptic members 38 and the optic 12, thereby preventing PCO.

As mentioned above, the contact surface 24 of the enlarged distal region 20 has a large surface area, thereby providing a large surface area subject to cellular and fibrous growth. For example, each of the contact surfaces 24 of the enlarged distal region 20 may have an axial length l (or arcuate span λ) of at least about 1 mm and preferably on the order of about 2 mm. Therefore, depending upon the radius of the IOL 10, each of the contact surfaces 24 may have a surface area of the product of the axial length l and the arc length a.

Contact of the IOL 10 with the capsular bag 28 is further enhanced by disposing the enlarged distal region 20 in a perpendicular manner to the haptic members 38. Accordingly, the contact surface 24 is substantially parallel to the optical axis 10 of the IOL 10. The axial disposition of the enlarged contact surface 24 within the capsular bag 28 increases the retention of the IOL 10 therewithin, particularly immediately following implantation.

Post-operative cellular and fibrous growth of the interior of the capsular bag 28 to the enlarged distal region 20 of the movement assembly 14 enables the IOL 10 of the present invention to essentially fully function like a natural crystalline lens. The cellular and fibrous growth is facilitated by the close proximity of the contact surface 24 with the capsular bag 28.

To further facilitate this growth, the enlarged distal region 20 may include a plurality of depressions or holes 44. Each of the holes 44 provides a purchase on which cells and fibrin may grow. It is anticipated that this cellular and fibrous growth may take place within the first few weeks after the IOL 10 is implanted in an eye. Accordingly, the IOL 10 is permanently attachable to the capsular bag 28. This vigorous attachment of the IOL 10 to the capsular bag 28 ensures that the IOL 10 moves axially in direct response to changes in the capsular bag 28, therefore accommodating near vision, analogous to that of a natural crystalline lens.

Figure 4:
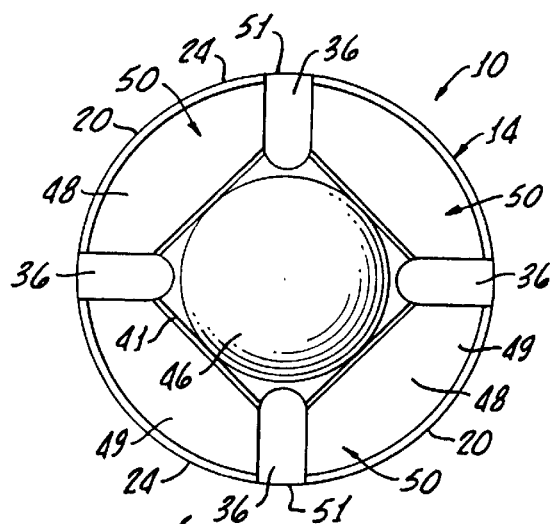
FIG. 4 is a plan view of an alternate embodiment of an intraocular lens (IOL) of the invention, illustrating the use of flexible structural material between movement members.

With continued reference to FIGS. 2 and 3 and additional reference to FIG. 4, the IOL 10 of the present invention may be configured as a two-optic IOL. More specifically, exemplary IOL 10 may include a secondary optic 46 coupled to a secondary member 48. Analogous to member 16 described above, the secondary member 48 may include a proximal region coupled to the secondary optic 46 and a distal region, which distal region is either the enlarged distal region 20 described above, or a separate enlarged distal region, as indicated in the region 49. Further, the plurality of cut-out regions 36 may extend through the secondary member 48, thereby defining a plurality of secondary haptic members 50.

The secondary member 48 with secondary optic 46 may be integral with the enlarged distal region 20 or, alternatively, may be mechanically attached to the enlarged distal region 20 or member 16 to function as an auxiliary IOL. In one useful embodiment, the enlarged distal region 20 of the first movement member 10 is provided with a groove or channel (not shown). The secondary movement member 48 is adapted to fit into the groove, thereby holding the second optic 46 in position in the eye.

Figure 5:
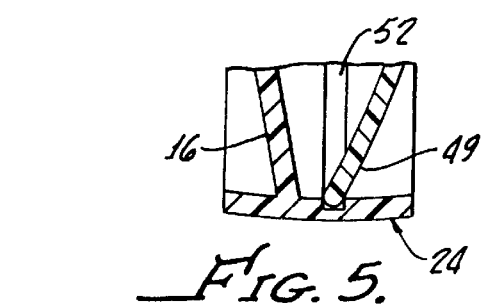
FIG. 5 is an enlarged view of a two-lens system and a circumferential groove for receiving and retaining a posterior lens.

More specifically, the distal regions 49 of the secondary haptic members 50 may be adapted to attach to or be retained by the movement assembly 14 of the IOL 10. For example, a groove may be formed either on a posterior side of member 16 or, alternatively, on an interior side of the enlarged distal region 24. The latter type of groove is seen at 52 in FIG. 5. The groove 52 is sized so that ends of the distal regions 49 of the secondary haptic members 50 are receivable therein. The distal regions 49 may be permanently received within the groove 52 such as with adhesive or, alternatively, releasably received so that the secondary optic 46 may be replaced if needed or desired.

Analogous to the haptic members 38 described above, secondary haptic members 50 are angulated such that the secondary optic 46 is positioned posterior to respective intersections of the haptic members and the enlarged distal regions 20, which is particularly shown in FIG. 2. For the purposes of this description, this angled configuration of the secondary haptic members 50 will be called "posterior angulation." By angulating the secondary haptic members 50 in this anterior manner, the movement assembly 14 is biased to move the secondary optic 46 toward the posterior of the eye 30 when the ciliary muscle 32 contracts.

In one useful embodiment each of the plurality of cut-out regions 36 in the secondary member 48 is at least partially filled with or covered by a structural material 51 having increased flexibility relative to the movement member. Thus, the second IOL is prevented from buckling while, at the same time the structural material 51 is effective to at least inhibit cell growth from the capsular bag onto the optic. This structural material 51 may have the same chemical make-up as the proximal regions of the movement members and have a reduced thickness relative to the proximal regions to provide the increased flexibility. In particular, the cut-out regions 36 may be filled with the same material from which the optic 46 is made.

Figure 6:
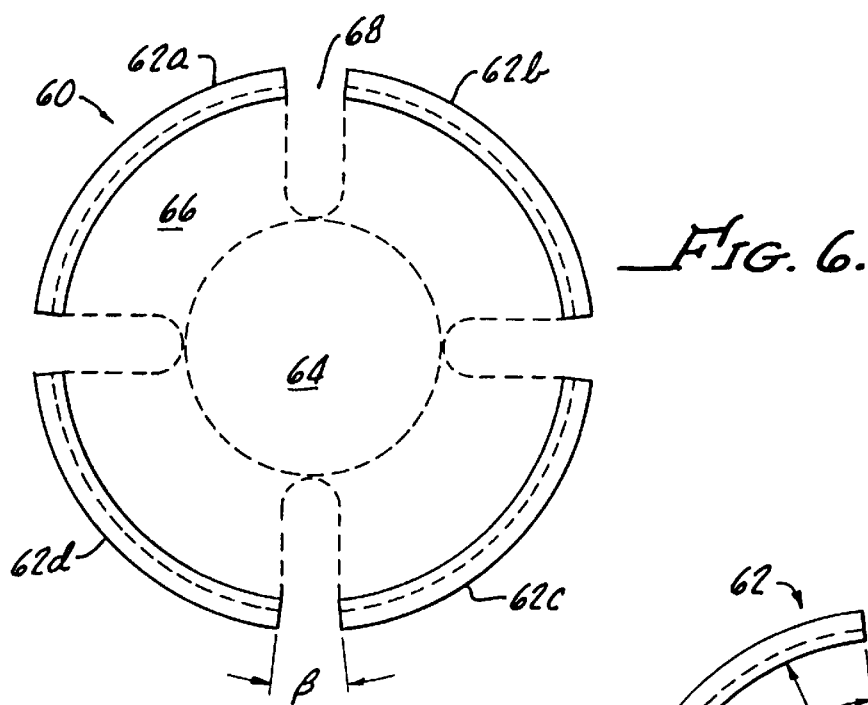
FIG. 6 is a plan view of and alternative embodiment of an intraocular lens (IOL) of the invention constructed of mechanically coupled lens and peripheral regions.
Figure 7A:
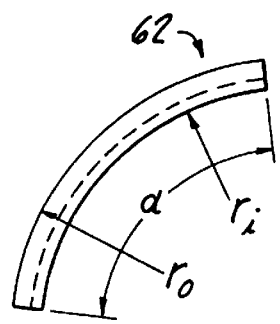
FIG. 7A is a plan view of one segment of a peripheral region of the IOL of FIG. 6.

FIG. 6 illustrates an alternative embodiment of the present invention in which an intraocular lens (IOL) 60 comprises an inner lens portion mechanically coupled to an outer peripheral region 62. In FIG. 6, the inner lens portion is shown in phantom and includes an optic 64 and a plurality of movement members 66 extending radially outwardly therefrom. As with the earlier embodiments, there are four such movement members 66 extending radially outward evenly about the optic 64, and each defining an included angle of nearly 90°.

As seen in FIGS. 6 and 7A–C, the outer peripheral region 62 comprises a plurality of individual arcuate segments 62a–d disposed around the periphery of the IOL and each mechanically coupled to a movement member 66. In the illustrated embodiment, the movement member 66 are substantially pie-shaped and each of the arcuate segments 62 has a length that matches the outer circumferential arc of the respectively coupled movement member. Desirably, the included angle of each movement member 66 and coupled peripheral segment 62 is less than 90° so that cut-outs or spacer regions 68 are defined therebetween. In addition, the arc of the each segment 62 is desirably centered at the optical axis of the optic 64. As previously described, the spacer regions 68 each extend from the peripheral region 62 to the optic 64, and terminate at a radially inner curved end.

Various dimensions of each segment 62 are illustrated in the drawings and exemplary values provided herein. In a preferred embodiment, each of the arcuate segments 62 defines an included angle a of between 70–85°, and more particularly about 78°. Consequently, the angle β defined between the segments is between about 5–20°, and more particularly about 12°. The exemplary embodiment has an outer radius $r_o$ of about 5.27 mm (0.2075 inches) and an inner radius $r_i$ of about 4.76 mm (0.187 inches).

Figure 7B:
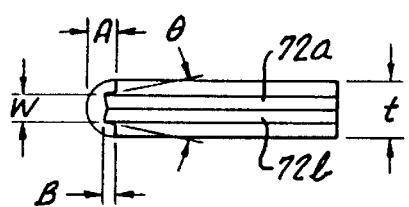
FIG. 7B is an elevational view of the peripheral region segment of FIG. 7A.
Figure 7C:
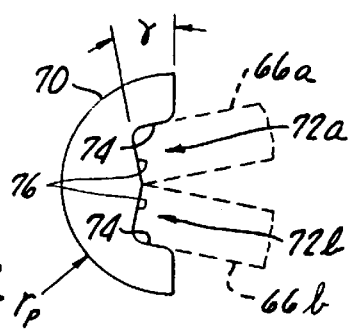
FIG. 7C is an enlarged view of a portion of FIG. 7B.

With reference particularly to FIGS. 7B and 7C, each of the arcuate segments 62 includes a rounded outer surface 70 and a pair of grooves 72a and 72b defined on the inner surface. Each groove 72 is defined by a side wall 74, and a peripheral wall 76. The side walls 74 of the two grooves diverge but generally face each other, and the peripheral walls 76 are angled with respect one another and meet at an apex 78, desirably at the axial midplane of the segment 62.

Again, particular dimensions are shown in the drawings, with certain exemplary values provided herein. In particular, the axial thickness t of each arcuate segment 62 is about 1.02 mm (0.04 inches), while the outer peripheral radius $r_p$ is desirably about the same as the thickness t, namely about 1.02 mm (0.04 inches). The overall radial thickness A of each segment 62 is about 0.51 mm (0.02 inches), while the radial depth B of each of the grooves 72 is about 0.23 mm (0.009 inches). The axial width w of the two grooves 72 together is about 0.51 mm (0.02 inches), and the peripheral surface 76 of each groove defines an angle γ of about 10° at any one point with respect to a plane tangent to the entire arcuate segment 62 at that point. Finally, the included angle θ defined by the divergent side walls 74 of the two grooves 72 is about 20°.

Because there are two grooves 72a,b, each arcuate segment 62 receives movement members 66 extending outward from two different optics 64. More particularly, FIG. 7C illustrates two movement members 66a and 66b disposed, respectively, within the grooves 72a and 72b and diverging at the included angle θ of the side walls 74. In other words, one of the optics is anteriorly vaulted and the other optic is posteriorly vaulted. The two movement members 66a,b are desirably sized to precisely fit within grooves 72a,b and contact at juxtaposed corners coincident with the apex 78. The resulting two-optic system can be customized to suit a wide variety of patient needs.

Figure 8:
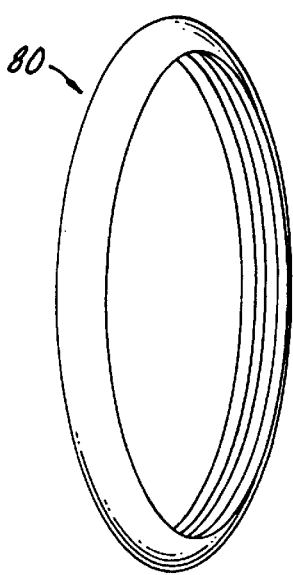
FIG. 8 is a perspective view of a ring formed during the process of making the peripheral region of the IOL of FIG. 6.

In a preferred manufacturing process, the segments 62a–d are formed from a circular ring 80 as seen in FIG. 8. In particular, the ring 80 is molded using conventional means, and the segments 62 are then machined therefrom. Subsequently, the segments 62 are mechanically coupled to the respective movement members 66 using a suitable adhesive, or the like. Those of skill in the art will understand that there are various means other than adhesives for attaching movement members to peripheral structures. As a result, the IOL 60 has the benefit of an enlarged outer peripheral region 62 which helps distribute forces imparted by the ciliary muscles to the movement members 66, and thereafter to the optic 64. Such a force distribution system helps improve accommodation of the IOL 60.

The optics 12 and 46 may be constructed of rigid biocompatible materials such as polymethyl methacrylate (PMMA) or deformable materials such as silicone polymeric materials, acrylic polymeric materials, hydrogel polymeric materials, and the like. The deformable materials allow the IOL 10 to be rolled or folded for insertion through a small incision into the eye. Although the optic 12 as shown is a refractive lens body, the present IOLs may include a diffractive lens body, and such embodiment is included within the scope of the present invention.

The optic 12 may be either integral with or mechanically coupled to the member 16. The member 16 may be constructed of the same or different biocompatible materials as the optic 12, and is preferably made of polymeric materials such as polypropylene, silicone polymeric materials, acrylic polymeric materials, and the like. The movement assembly 14 is preferably deformable in much the same manner as the optic 12 to facilitate the passage of the IOL 10 through a small incision into the eye. The material or materials of construction from which the movement assembly 14 is made are chosen to provide the assembly with the desired mechanical properties, e.g., strength and deformability, to meet the needs of the particular application involved.

The IOL 10 may be inserted into the capsular bag 28 of a mammalian eye using conventional equipment and techniques, for example, after the natural crystalline lens is removed using a phaceomulsification technique. The IOL 10 is preferably rolled or folded prior to insertion into the eye so as to fit through a small incision, for example, on the order of about 3.2 mm. After insertion, the IOL 10 may be positioned in the eye as shown in FIG. 2.

If the IOL 10 is to be implanted in an adult human eye, the optic 12 preferably has a diameter in the range of about 3.5 mm to about 7 mm and, more preferably, in the range of about 5 mm to about 6 mm. Further, the IOL 10 may have an overall diameter, with the movement assembly 14 in an unstressed condition, of about 8 mm to about 11 mm or 12 mm. Additionally, the optic 12 preferably has a far-vision correction power for infinity in an accommodated state.

The present invention provides accommodating IOLs and methods for using such IOLs. The IOLs of the invention are configured to reduce the stretching of the capsular bag, to maintain the elasticity and/or integrity of the capsular bag, to enhance the effectiveness of the eye, particularly the function of the ciliary muscle and the zonules. The present IOLs promote the secure retention within the capsular bag by providing an enlarged contact surface to which cells and fibrin may grow. In addition, the present IOLs inhibit PCO. These benefits are obtained with IOLs which are streamlined in construction and relatively easy to manufacture and insert into the eye and which effectively provide accommodation for long-term use.

While the present invention has been described with respect to various specific examples and embodiments, it is to be understood that the invention is not limited thereto and that it can be variously practiced within the scope of the following claims.

What is claimed is:

1. An intraocular lens comprising:
   an optic adapted to focus light to a retina of an eye and having a central optical axis;
   a movement assembly coupled to the optic and adapted to cooperate with the eye to effect accommodating movement of the optic;
   the movement assembly including a plurality of movement members each having a proximal region coupled to the optic and an enlarged distal region; and
   each of the enlarged distal regions is formed separately from and mechanically coupled to the proximal region of that movement member, and has a contact surface adapted to be in contact with a peripheral region of a capsular bag of an eye.

2. The intraocular lens of claim 1, wherein the optic and the proximal region of each movement member are integrally formed, and the plurality of movement members are circumferentially spaced apart.

3. The intraocular lens of claim 2, wherein each distal region comprises an arcuate segment having at least one groove for receiving and mechanically coupling to a proximal region of a movement member.

4. The intraocular lens of claim 3, wherein each arcuate segment includes a pair of grooves each for receiving and mechanically coupling to a proximal region of a movement member, the intraocular lens being a two-optic lens.

5. The intraocular lens of claim 1, wherein the enlarged distal region of each movement member is mechanically coupled to the proximal region of that movement member using adhesive.

6. An intraocular lens comprising:
an optic adapted to focus light to a retina of an eye and having a central optical axis;
a movement assembly coupled to the optic and adapted to cooperate with the eye to effect accommodating movement of the optic; and
the movement assembly including at least one movement member having a proximal region coupled to the optic, the at least one movement member extending radially outwardly from the optic and including an enlarged distal region having a contact surface adapted to be in contact with a peripheral region of a capsular bag of an eye, and including a plurality of through holes extending through the contact surface.

7. The intraocular lens of claim 6 wherein the movement assembly is adapted and configured to fit within the capsular bag of a human eye.

8. The intraocular lens of claim 6 wherein the enlarged distal region is configured so that the contact surface is substantially coaxial with the optical axis of the optic.

9. The intraocular lens of claim 6 wherein the movement assembly includes a plurality of the movement members circumferentially spaced apart.

10. An intraocular lens comprising:
an optic adapted to focus light to a retina of an eye and having a central optical axis;
a movement assembly coupled to the optic and adapted to cooperate with the eye to effect accommodating movement of the optic;
the movement assembly including at least one movement member having a proximal region coupled to the optic, the at least one movement member extending radially outwardly from the optic and including an enlarged distal region having a contact surface adapted to be in contact with a peripheral region of a capsular bag of an eye; and
a second optic coupled to the movement assembly.

11. The intraocular lens of claim 10 wherein the movement assembly is adapted and configured to fit within the capsular bag of a human eye.

12. The intraocular lens of claim 10 wherein the movement assembly includes a plurality of the movement members circumferentially spaced apart.

13. The intraocular lens of claim 10 further comprising at least one haptic member coupled to the second optic and the distal region of the at least one movement member, and the second optic is separate from the optic.

14. The intraocular lens of claim 13 wherein, with the intraocular lens at rest, the optic is anteriorly vaulted and the secondary optic is posteriorly vaulted.

15. An intraocular lens comprising:
an optic adapted to focus light to a retina of an eye and having a central optical axis;
a movement assembly coupled to the optic and adapted to cooperate with the eye to effect accommodating movement of the optic; and
a second optic coupled to the movement assembly;
the movement assembly including a plurality of movement members each having a proximal region coupled to the optic and an enlarged distal region; and
each of the enlarged distal regions having a contact surface with a length parallel to the cental optical axis of at least about 1 mm and adapted to be in contact with a peripheral region of a capsular bag of an eye.

16. The intraocular lens of claim 15 wherein the movement assembly is positioned relative to the optic so that, with the intraocular lens at rest, the optic is anteriorly vaulted.

17. The intraocular lens of claim 15 wherein the movement assembly is adapted to fit within the capsular bag of a human eye.

18. The intraocular lens of claim 15 wherein each of the enlarged distal regions is configured such that the contact surface and the corresponding proximal region include longest dimensions oriented at different angles relative to the central optical axis.

19. The intraocular lens of claim 15 wherein each of the enlarged distal regions is configured such that the contact surface thereof is substantially parallel with the optical axis of the optic.

20. The intraocular lens of claim 15 wherein each of the enlarged distal regions is configured such that the contact surface thereof is substantially rounded.

21. The intraocular lens of claim 15 which is deformable to be passed through a small incision for insertion into an eye.

22. The intraocular lens of claim 15 wherein each of the plurality of movement members includes a hinge disposed proximally of the enlarged distal region.

23. The intraocular lens of claim 15, wherein each of the proximal regions is joined to one of the distal regions so that one or more sharp edges are present therebetween.

24. An intraocular lens comprising:
an optic adapted to focus light to a retina of an eye and having a central optical axis; and
a movement assembly coupled to the optic and adapted to cooperate with the eye to effect accommodating movement of the optic;
the movement assembly including at least one movement member having a proximal region coupled to the optic, the at least one movement member increasing in size while extending radially outwardly from the optic and including an enlarged distal region having a contact surface adapted to be in contact with a peripheral region of a capsular bag of an eye,
wherein the enlarged distal region includes a plurality of through holes extending through the contact surface.

* * * * *